(12) United States Patent
Scopton et al.

(10) Patent No.: US 9,149,173 B2
(45) Date of Patent: Oct. 6, 2015

(54) MEDICAL DEVICE FOR USE IN ENDOSCOPIC PROCEDURE

(75) Inventors: Paul M. Scopton, Winchester, MA (US);
Gary J. Leanna, Holden, MA (US);
Mark Wood, Watertown, MA (US);
Kurt A. E. Geitz, Sudbury, MA (US);
M. Kevin Richardson, Hopkinton, MA (US); Oscar R. Carrillo, Jr., Attleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1542 days.

(21) Appl. No.: 11/471,226

(22) Filed: Jun. 20, 2006

(65) Prior Publication Data
US 2007/0293719 A1    Dec. 20, 2007

(51) Int. Cl.
*A61B 1/00* (2006.01)
*A61M 5/178* (2006.01)
*A61M 5/14* (2006.01)
*A61B 1/018* (2006.01)
*A61B 17/34* (2006.01)

(52) U.S. Cl.
CPC ............. *A61B 1/018* (2013.01); *A61B 1/00098* (2013.01); *A61B 2017/347* (2013.01)

(58) Field of Classification Search
USPC ......... 600/104, 106, 107, 129, 149, 114–116, 600/121–125, 127, 153, 154; 604/256, 604/101.01–101.05, 96.01, 165.01–165.04, 604/103.04; 606/191–197
See application file for complete search history.

(56) References Cited

U.S. PATENT DOCUMENTS

| | | |
|---|---|---|
| 2,919,697 A | 1/1960 | Kim |
| 4,166,468 A | 9/1979 | Haynie |
| 4,285,341 A | 8/1981 | Pollack |
| 4,445,892 A | 5/1984 | Hussein et al. |
| 4,606,347 A | 8/1986 | Fogarty et al. |
| 4,730,616 A | 3/1988 | Frisbie et al. |
| 4,771,777 A | 9/1988 | Horzewski et al. |
| 4,798,193 A | 1/1989 | Giesy et al. |
| 4,820,271 A | 4/1989 | Deutsch |
| 4,820,349 A | 4/1989 | Saab |
| 4,827,941 A | 5/1989 | Taylor et al. |
| 4,832,028 A | 5/1989 | Patel |
| 4,838,268 A | 6/1989 | Keith et al. |
| 4,844,092 A | 7/1989 | Rydell et al. |
| 4,846,174 A | 7/1989 | Willard et al. |

(Continued)

FOREIGN PATENT DOCUMENTS

| | | |
|---|---|---|
| EP | 0 066 120 A2 | 12/1982 |
| EP | 0380227 A2 | 8/1990 |

(Continued)

OTHER PUBLICATIONS

Brugge, William R. et al., "Medical Progress: Pancreatic and Biliary Endoscopy," New England Journal of Medicine, vol. 341, No. 24, Dec. 9, 1999, pp. 1808-1816.

(Continued)

*Primary Examiner* — Ryan Henderson
(74) *Attorney, Agent, or Firm* — Bookoff McAndrews, PLLC

(57) ABSTRACT

Endoscopes and methods for making and using endoscopes. An example endoscope includes a handle portion and a shaft portion. The shaft portion may include one or more channels. A catheter and/or wire locking member may be coupled to a channel.

24 Claims, 17 Drawing Sheets

(56) References Cited

U.S. PATENT DOCUMENTS

| | | |
|---|---|---|
| 4,881,547 A | 11/1989 | Danforth |
| 4,917,102 A | 4/1990 | Miller et al. |
| 4,932,959 A | 6/1990 | Horzewski et al. |
| 4,944,740 A | 7/1990 | Buchbinder et al. |
| 4,976,689 A | 12/1990 | Buchbinder et al. |
| 5,040,548 A | 8/1991 | Yock |
| 5,090,959 A * | 2/1992 | Samson et al. ................ 600/116 |
| 5,360,403 A * | 11/1994 | Mische .................... 604/101.02 |
| 5,855,569 A * | 1/1999 | Komi ............................ 604/526 |
| 5,921,971 A | 7/1999 | Agro et al. |
| 5,938,585 A | 8/1999 | Donofrio |
| 6,007,522 A | 12/1999 | Agro et al. |
| 6,096,009 A | 8/2000 | Windheuser et al. |
| 6,152,910 A | 11/2000 | Agro et al. |
| 6,251,084 B1 * | 6/2001 | Coelho ......................... 600/585 |
| 6,270,465 B1 | 8/2001 | Keith et al. |
| 6,277,065 B1 | 8/2001 | Donofrio |
| 6,299,628 B1 | 10/2001 | Harrison et al. |
| 6,312,404 B1 | 11/2001 | Agro et al. |
| 6,346,093 B1 | 2/2002 | Allman et al. |
| 6,443,912 B1 | 9/2002 | Mazzola et al. |
| 6,464,632 B1 * | 10/2002 | Taylor ........................... 600/139 |
| 6,520,951 B1 | 2/2003 | Carrillo, Jr. et al. |
| 6,582,401 B1 | 6/2003 | Windheuser et al. |
| 6,606,515 B1 | 8/2003 | Windheuser et al. |
| 6,663,597 B1 | 12/2003 | Windheuser et al. |
| 6,746,442 B2 | 6/2004 | Agro et al. |
| 6,827,683 B2 | 12/2004 | Otawara |
| 6,869,416 B2 | 3/2005 | Windheuser et al. |
| 6,879,854 B2 | 4/2005 | Windheuser et al. |
| 6,997,908 B2 | 2/2006 | Carrillo, Jr. et al. |
| 7,060,052 B2 | 6/2006 | Windheuser et al. |
| 7,076,285 B2 | 7/2006 | Windheuser et al. |
| 2003/0114732 A1 | 6/2003 | Webler et al. |
| 2003/0181939 A1 * | 9/2003 | Bonutti ......................... 606/192 |
| 2004/0019377 A1 * | 1/2004 | Taylor et al. ................. 623/2.11 |
| 2004/0049095 A1 | 3/2004 | Goto et al. |
| 2005/0049455 A1 * | 3/2005 | Ootawara et al. ............. 600/107 |
| 2005/0143770 A1 | 6/2005 | Carter et al. |

FOREIGN PATENT DOCUMENTS

| | | | |
|---|---|---|---|
| EP | 0416734 A1 | 3/1991 | |
| EP | 1 709 900 A1 | 10/2006 | |
| JP | 2001275942 A * | 10/2001 | ............... A61B 1/00 |
| WO | 01/58360 A2 | 8/2001 | |

OTHER PUBLICATIONS

Internet Article: http://www.olympusamerica.com/msg_section/msg_product_print.asp?product=1144, "Olympus V-Scope(TM)—TJF—160VF," printed Aug. 1, 2005, 2 sheets.

Internet Article: http://www.olympusamerica.com/msg_section/vsys/vsys_faq.asp, "Frequently Asked Questions," printed Aug. 1, 2005, 2 sheets.

* cited by examiner

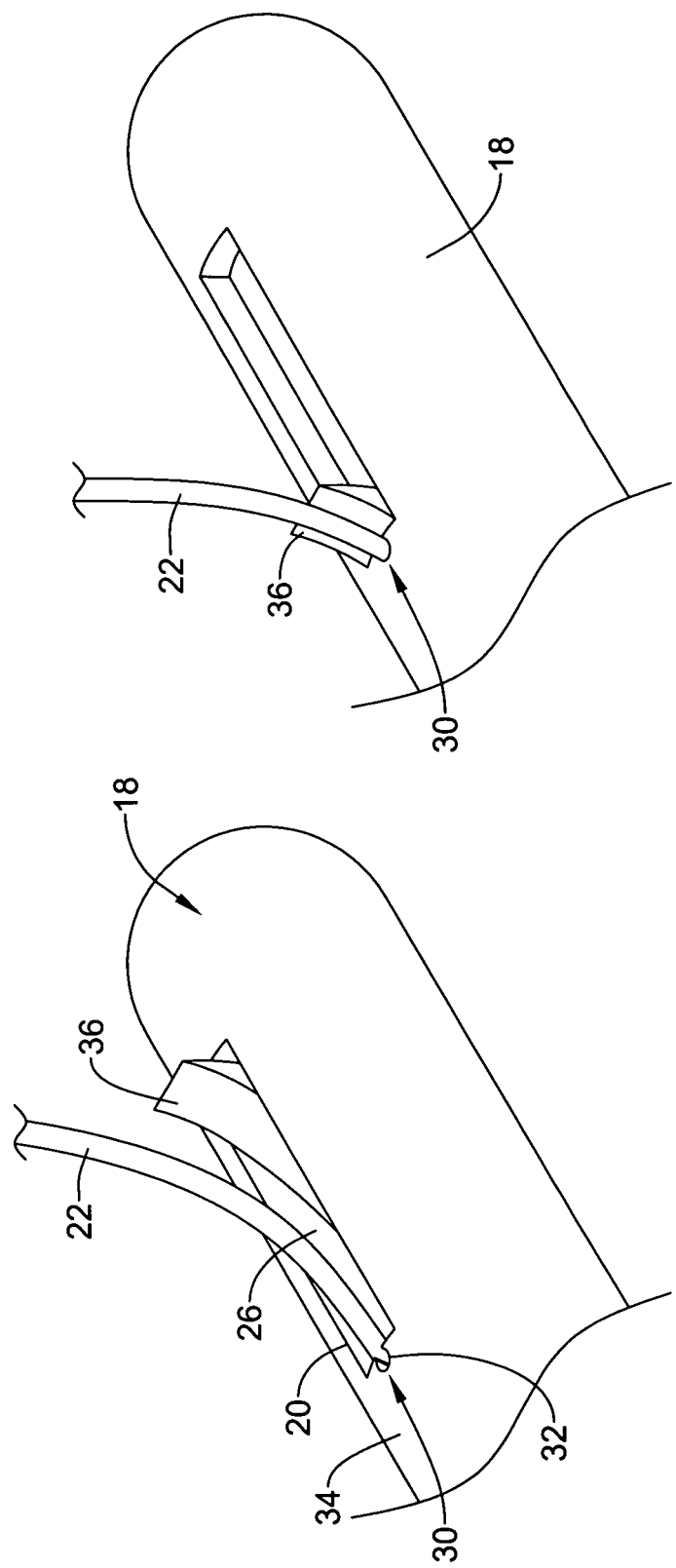

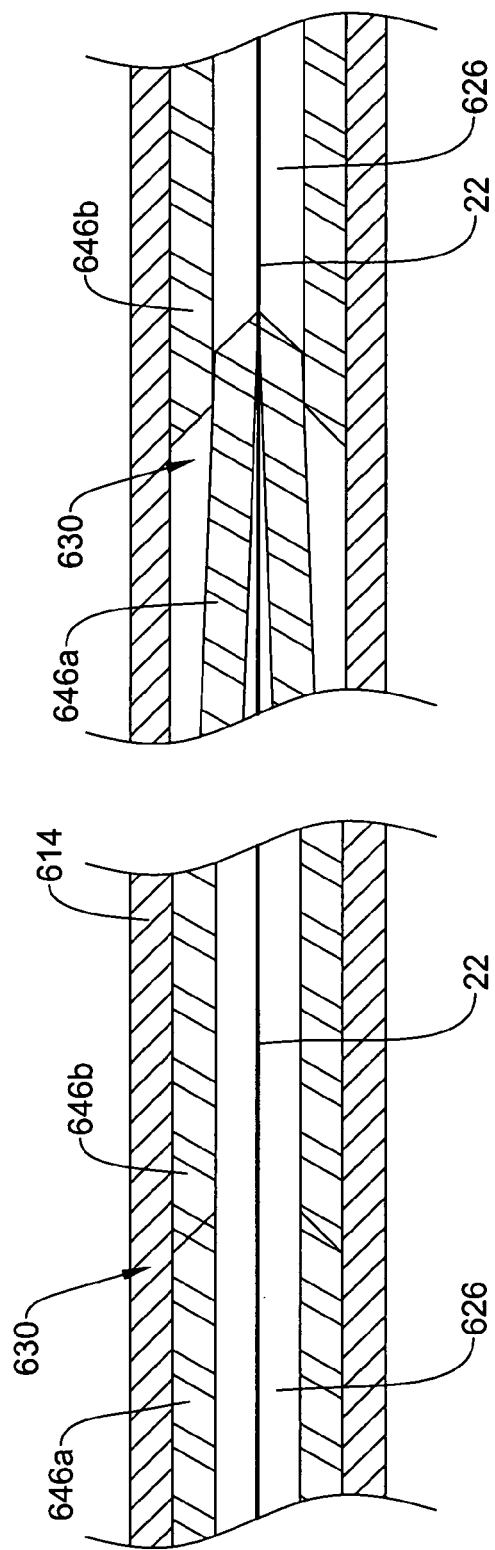

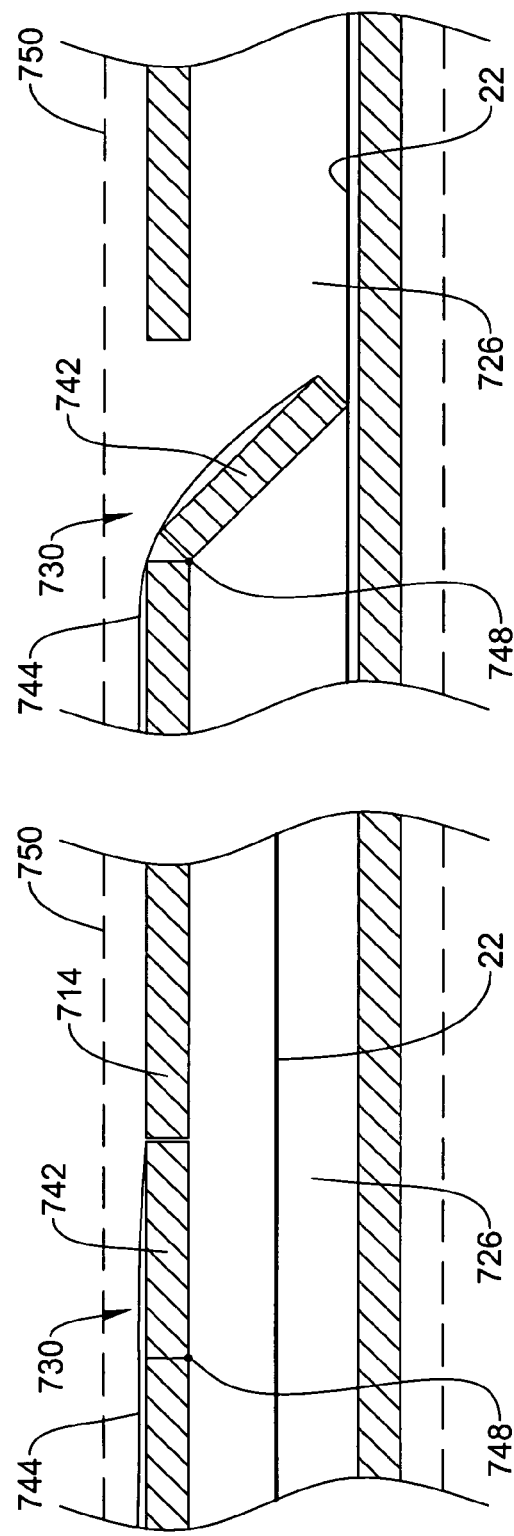

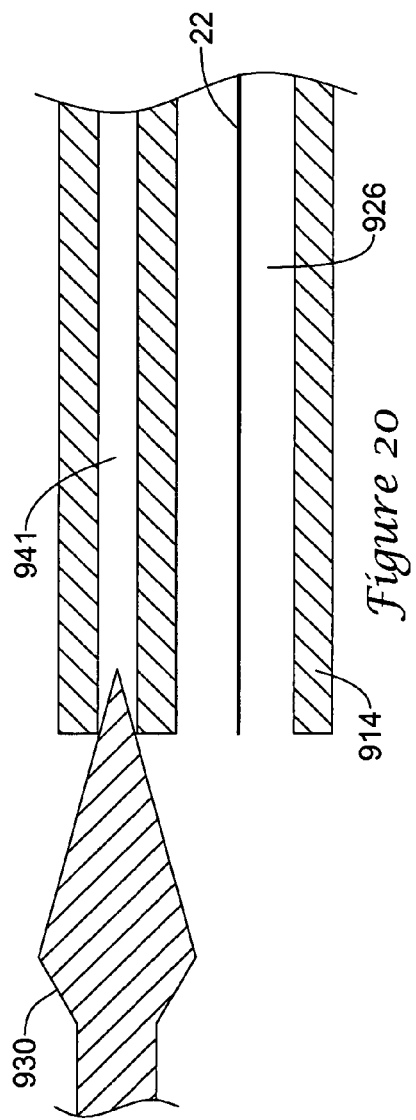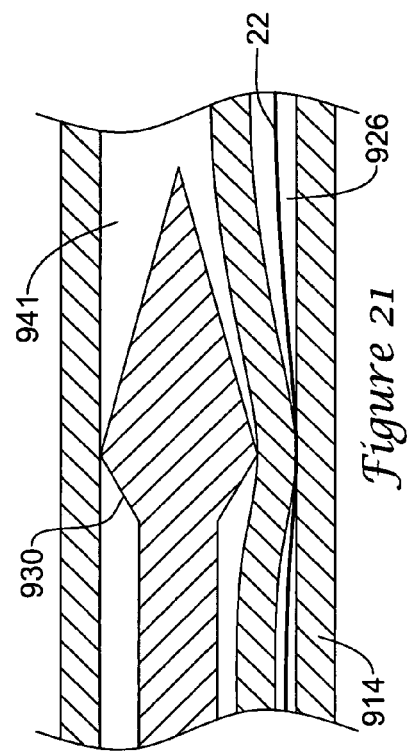

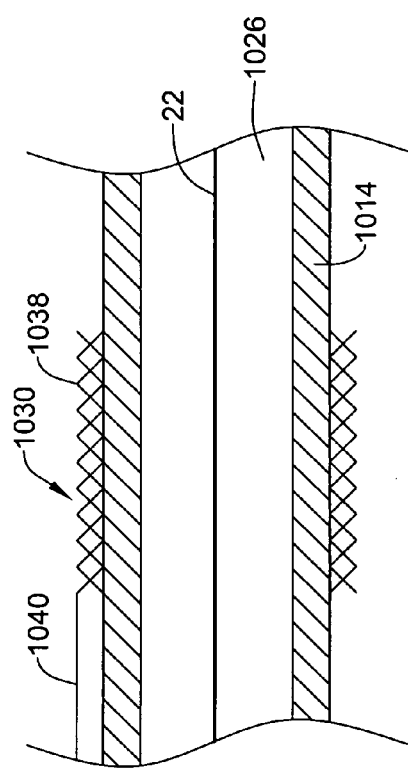
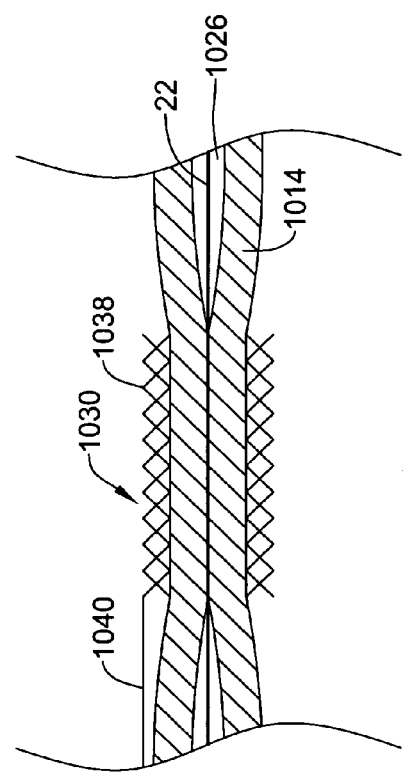

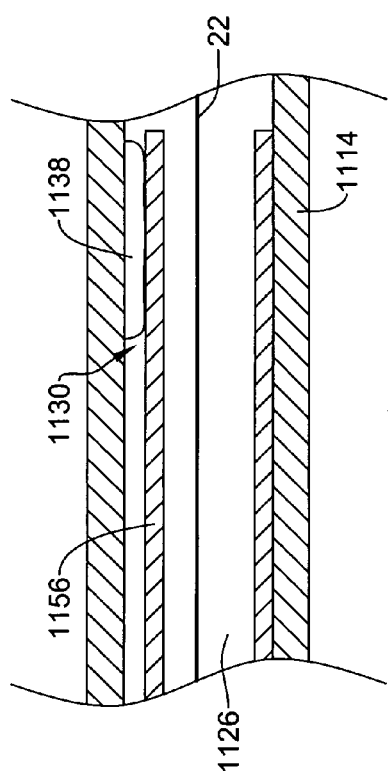
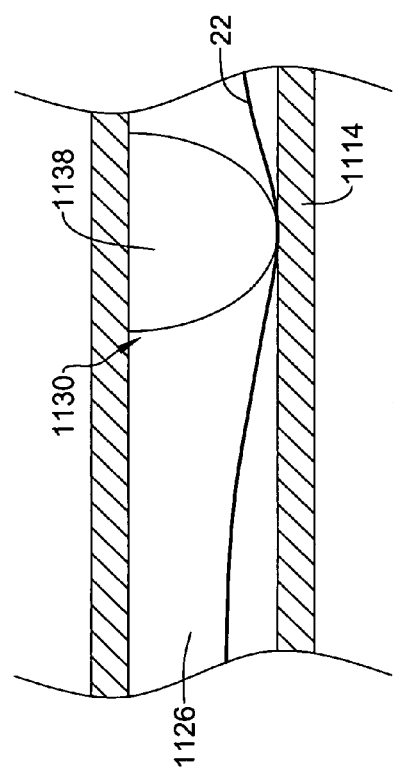

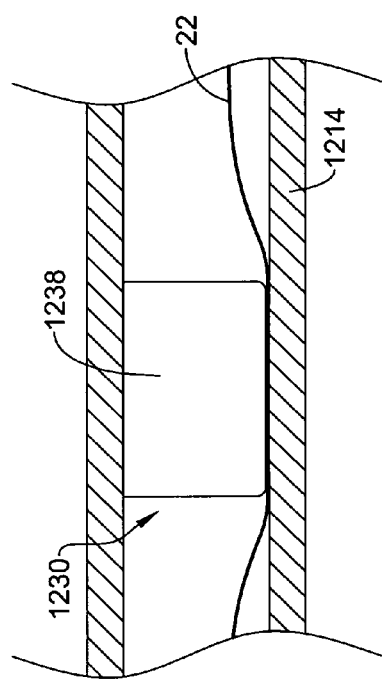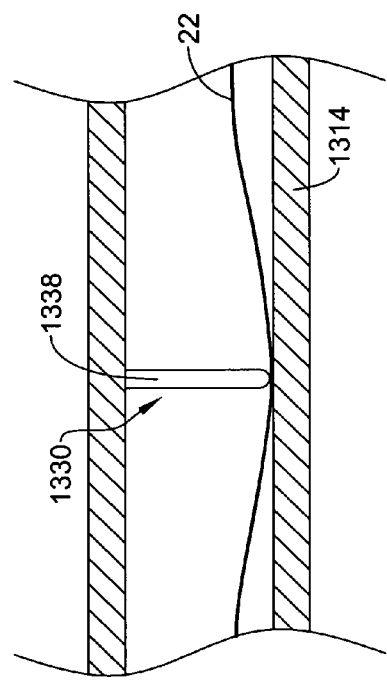

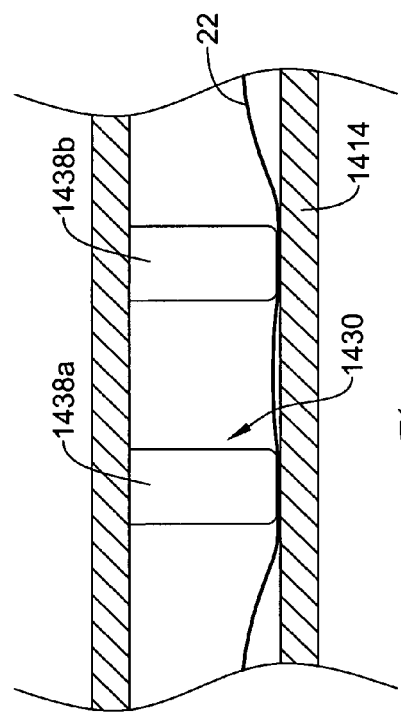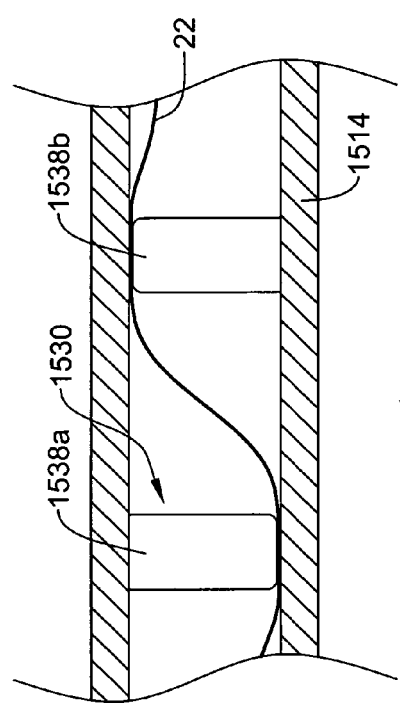

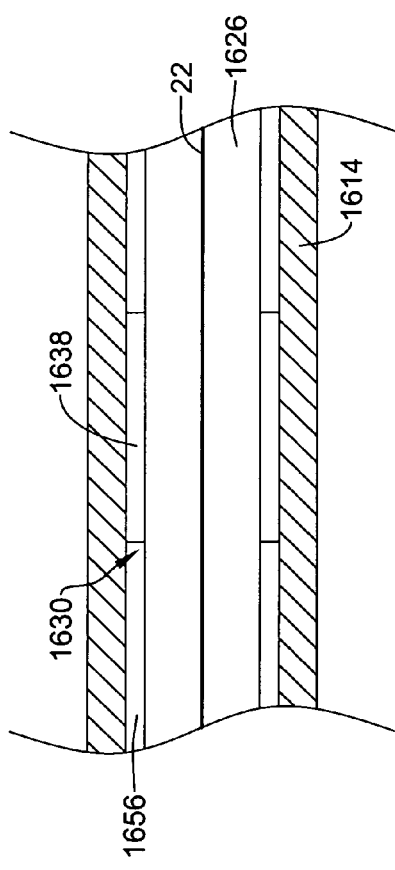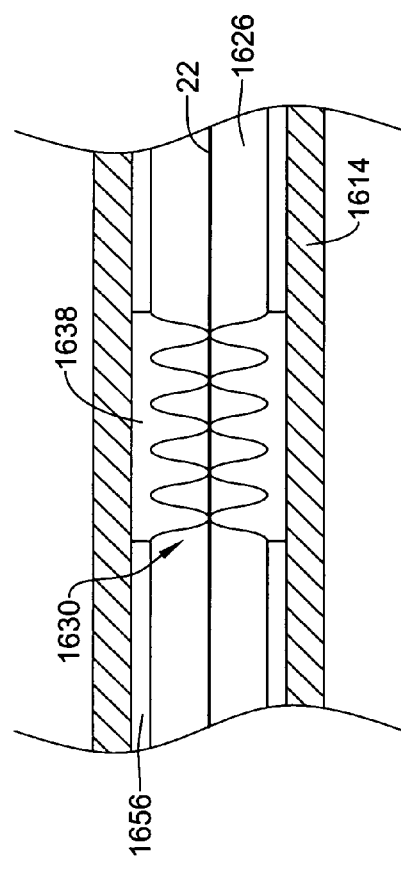

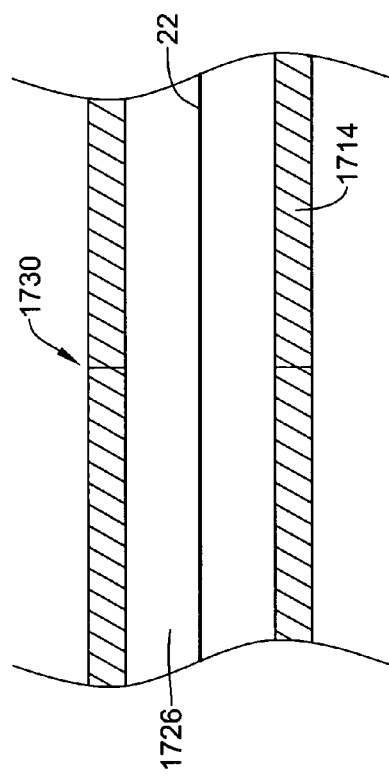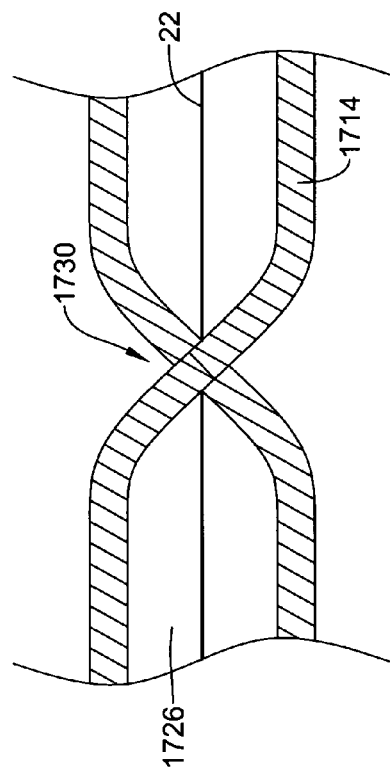

MEDICAL DEVICE FOR USE IN ENDOSCOPIC PROCEDURE

FIELD

The present invention pertains to endoscopes and methods for making and using endoscopes. More particularly, the present invention pertains to endoscopes that include a wire and/or catheter locking member.

BACKGROUND

A wide variety of endoscopes and endoscopic procedures have been developed. Of the known endoscopes and endoscopic procedures, each has certain advantages and disadvantages. There is an ongoing need to provide alternative endoscopes as well as methods for making and using endoscopes.

SUMMARY

The invention provides design, material, and manufacturing method alternatives for endoscopes and for methods for making and using endoscopes. An example endoscope includes a handle portion and a shaft portion. The shaft portion may include one or more channels. A catheter and/or wire locking member may be coupled to a channel. The locking member can be actuated to secure the position of a medical device disposed in a channel. Additional details regarding these and other embodiments are described in more detail below.

The above summary is not intended to describe each disclosed embodiment or every implementation of the present disclosure. The Figures and Detailed Description which follow more particularly exemplify these embodiments.

BRIEF DESCRIPTION OF THE DRAWINGS

The disclosure may be more completely understood in consideration of the following detailed description of various embodiments of the disclosure in connection with the accompanying drawings, in which:

FIG. 2 is a perspective view of an illustrative locking member of an endoscopic instrument assembly;

FIG. 3 is a perspective view of the illustrative locking member of FIG. 2 where the locking member is securing the position of a medical device;

FIG. 14 is a partial cross-sectional side view of another illustrative locking member of an endoscopic instrument assembly;

FIG. 15 is a partial cross-sectional side view of the illustrative locking member of FIG. 14 where the locking member is securing the position of a medical device;

FIG. 16 is a partial cross-sectional side view of another illustrative locking member of an endoscopic instrument assembly;

FIG. 17 is a partial cross-sectional side view of the illustrative locking member of FIG. 16 where the locking member is securing the position of a medical device;

FIG. 20 is a partial cross-sectional side view of another illustrative locking member of an endoscopic instrument assembly;

FIG. 21 is a partial cross-sectional side view of the illustrative locking member of FIG. 20 where the locking member is securing the position of a medical device;

FIG. 22 is a partial cross-sectional side view of another illustrative locking member of an endoscopic instrument assembly;

FIG. 23 is a partial cross-sectional side view of the illustrative locking member of FIG. 22 where the locking member is securing the position of a medical device;

FIG. 24 is a partial cross-sectional side view of another illustrative locking member of an endoscopic instrument assembly;

FIG. 25 is a partial cross-sectional side view of the illustrative locking member of FIG. 24 where the locking member is securing the position of a medical device;

FIG. 26 is a partial cross-sectional side view of another illustrative locking member securing the position of a medical device;

FIG. 27 is a partial cross-sectional side view of another illustrative locking member securing the position of a medical device;

FIG. 28 is a partial cross-sectional side view of another illustrative locking member securing the position of a medical device;

FIG. 29 is a partial cross-sectional side view of another illustrative locking member securing the position of a medical device;

FIG. 30 is a partial cross-sectional side view of another illustrative locking member of an endoscopic instrument assembly;

FIG. 31 is a partial cross-sectional side view of the illustrative locking member of FIG. 30 where the locking member is securing the position of a medical device;

FIG. 32 is a partial cross-sectional side view of another illustrative locking member of an endoscopic instrument assembly; and FIG. 33 is a partial cross-sectional side view of the illustrative locking member of FIG. 32 where the locking member is securing the position of a medical device.

DETAILED DESCRIPTION

Figure 1:
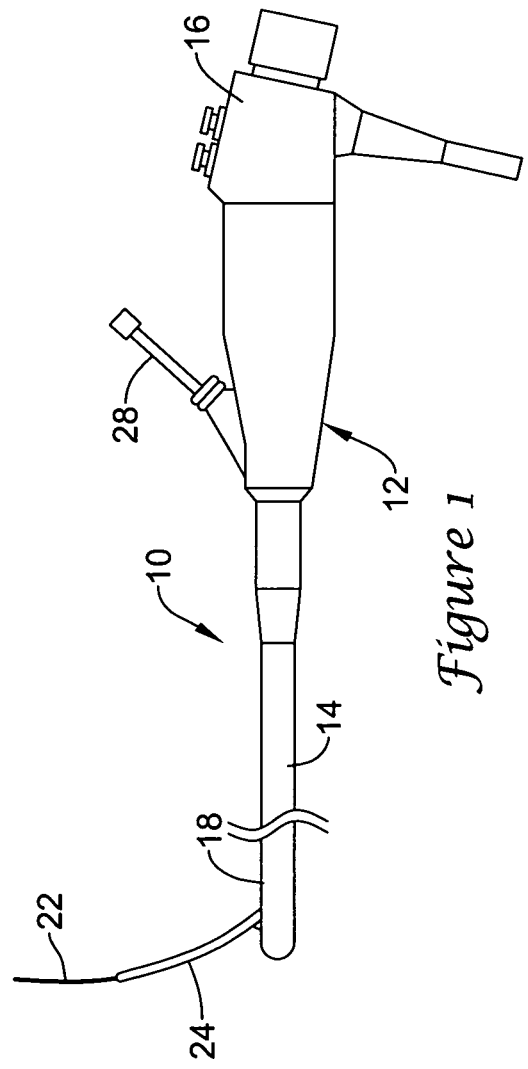
FIG. 1 is a side elevation view of an illustrative endoscopic instrument assembly.

The following Detailed Description should be read with reference to the drawings in which similar elements in different drawings are numbered the same. The drawings, which are not necessarily to scale, depict illustrative embodiments and are not intended to limit the scope of the invention.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

A vast number of endoscopic devices exist that have a wide variety of applications. In at least some applications, the position of the endoscopic device and/or the position of a particular medical device disposed in the endoscopic device is important. This is at least partially due to challenges in precisely navigating the endoscope or endoscopic instruments through the anatomy of a patient. For example, when an endoscope and medical device disposed in a working channel therein are used for biliary applications, it may be difficult to advance the medical device through the papilla of Vater and toward the bile duct. Moreover, once a device is successfully advanced through the papilla of Vater, subtle movement of the device can result in the device being withdrawn back out from the papilla of Vater, necessitating another round of skilled maneuvering in order to proceed with the intervention.

Because of this potential complication, a number of endoscopes include (e.g., as an accessory to the endoscope) a proximal "wire lock" outside of the patient or similar means for maintaining the position of a guidewire or catheter disposed in the working channel of the endoscope. These devices are situated near the handle of the endoscope, near the opening of the working channel.

For a number of reasons, it has been found to be desirable to lock a guidewire, catheter and/or other medical device in a different manner and using a different structure, for example near the distal end of the endoscope. This is because a guidewire or other medical device disposed in a working channel may not be fully taut or may have a small amount of "slack", which could shift in position and potentially displace the guidewire from the papilla of Vater. A proximal locking means, thus, may not account for slack in the guidewire or other medical device and otherwise may not properly hold the position of the guidewire or other medical devices in desired applications.

FIG. 1 is an example endoscopic instrument assembly 10 that addresses this need as well as provides a number of desirable features. Assembly 10 includes an endoscope 12 having a shaft portion 14 and a handle portion 16. Shaft portion 14 includes a distal end region 18 and a distal port 20 (best seen in FIG. 2) where one or more medical devices (e.g., a guidewire 22 and/or a catheter 24) disposed within a working channel 26 (best seen in FIG. 2) formed in shaft portion 14 with medical devices capable of extending distally from distal port 20. An elevator 36 can be disposed adjacent port 20 that, when actuated, alters the angle at which guidewire 22 and/or catheter 24 exits port 20. Handle portion 16 includes one or more openings or a control region 28 where instruments (e.g., endoscopic instruments, guidewires, catheters, and the like) can gain access to working channel 26 and be extended through shaft portion 14 and out from port 20. Control region 28 may also include a control wire (not shown) for controlling elevator 36.

For the reasons stated above, it may be desirable for assembly 10 to include a locking means that is capable of securing the position of guidewire 22 and/or catheter 24. Turning now to FIG. 2, it can be seen that distal end region 18 of shaft portion 14 includes a locking member 30. According to this embodiment, locking member 30 takes the form of a notch or slot 32 formed in a side wall 34 of distal end region 18 and adjacent to distal port 20 (which is also formed in side wall 34). Notch 32 can take a number of different shapes (e.g., "V"-shaped, "U"-shaped, "C"-shaped, round, oval, polygonal, etc.) but is generally configured to house, for example, guidewire 22 in a manner that allows guidewire 22 to be secured from axial movement relative to the endoscope. Therefore, guidewire 22 can be held in place by actuating the elevator 36 so that elevator 36 presses against guidewire 22 (housed in notch 32) as shown in FIG. 3.

In use, endoscope 12 can be disposed in a body lumen. For example, shaft portion 14 can be advanced through the mouth and into the digestive tract of a patient. Once positioned, guidewire 22 can be advanced through working channel 26 to the desired target location. With guidewire 22 positioned, elevator 36 can be activated so that it raises and presses guidewire 22 into notch 32, thereby securing the position of guidewire 22. Catheter 24 can be advanced over guidewire 22 to the target region or, in some other embodiments, catheter 24 can be advanced through working channel 26 to the target region prior to advancing guidewire 22. Elevator 36 may be similarly utilized to press against catheter 24 to hold the position of catheter 24 while catheter 24 is disposed adjacent notch 32 or at any other suitable location. In addition, catheter 24 may be proximally withdrawn far enough to expose guidewire 22 so that elevator 36 can be used to secure guidewire 22. It can be appreciated that a number of variations to these generally stated methods are contemplated and can be utilized without departing from the spirit of the invention.

Figures 4, 5:
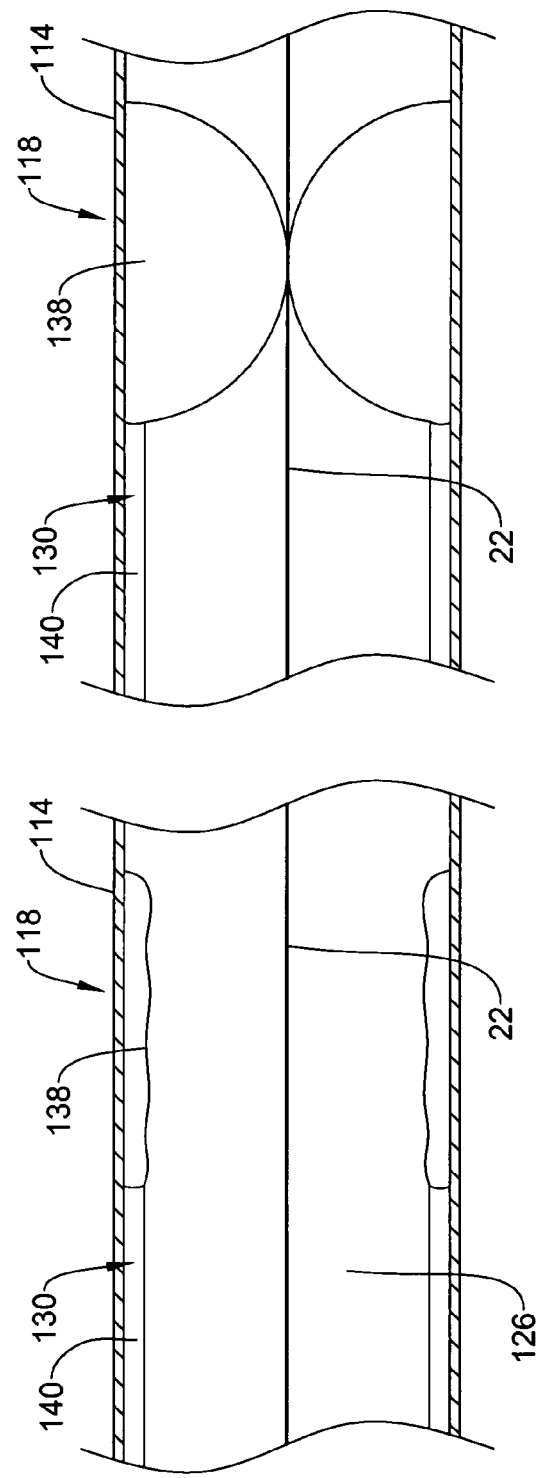
FIG. 4 is a partial cross-sectional side view of another illustrative locking member of an endoscopic instrument assembly.
FIG. 5 is a partial cross-sectional side view of the illustrative locking member of FIG. 4 where the locking member is securing the position of a medical device.

FIGS. 4-33 illustrate a number of different embodiments of endoscope locking members that can be used with assembly 10 or similarly configured endoscopic assemblies. Turning now to FIGS. 4 and 5, example endoscope locking member 130 is shown that includes an inflatable balloon or bladder 138 disposed within the working channel adjacent distal end region 118 of shaft portion 114 and one or more inflation conduits 140 coupled to balloon 138. According to this embodiment, inflation media can be infused through conduit 140 and into balloon 138 so that balloon 138 enlarges, as shown in FIG. 5, so as to secure the position of guidewire 22. This mechanism may be similarly utilized to secure the position of catheter 24 or any other suitable medical device. Deflating balloon 138 releases guidewire 22.

In some embodiments, balloon 138 is a single or multi-lobed balloon 138 that is coupled to one or more conduits 140.

Accordingly, guidewire 22 is captured within a small longitudinal channel defined through the middle of balloon 138. This embodiment may be desirable, for example, because it effectively centers guidewire 22 in working channel 126. Alternatively, balloon 138 may be configured to press guidewire 22 against an interior wall of shaft portion 114.

In some embodiments, balloon 138 and conduit 140 are fused to the inside surface of shaft portion 114. In addition, balloon 138 may be disposed within a notch or slot formed in the wall of shaft portion 114. In other embodiments, balloon 138 and conduit 140 comprise a separate component that can be slid into any suitable working channel so as to provide locking capabilities to essentially any endoscope. This embodiment desirably adds distal guidewire 22 locking capabilities to a number of different endoscopes.

In still other embodiments, balloon 138 may have a basket or cage (not shown) disposed on its outer surface. Alternatively, balloon 138 may be omitted in lieu of a basket or cage. In these later embodiments, the cage may be actuated in any suitable manner. For example, the cage may be made from a shape memory material (including nickel-titanium alloys, shape memory polymers, etc.) that can shift to a pre-set shape (e.g., to a shape where the basket expands into channel 126 and locks guidewire 22) when exposed to different thermal conditions. The changes in temperature may be achieved by any convenient mechanism such as through the use of electrical current, heated fluids, etc.

Embodiments that utilize a cage may also benefit from the fact that the cage can alter the surface of the locking member. This may aid the locking member in achieving a suitable "grip" on guidewire 22. A wide variety of other surface modifications are contemplated for the various locking members disclosed herein. For example, a locking member may include a surface that is roughened, includes ridges or threads, includes an adhesive or "sticky" material, and the like. Essentially any of the locking members disclosed herein can benefit from these or other surface modifications.

Figure 7:
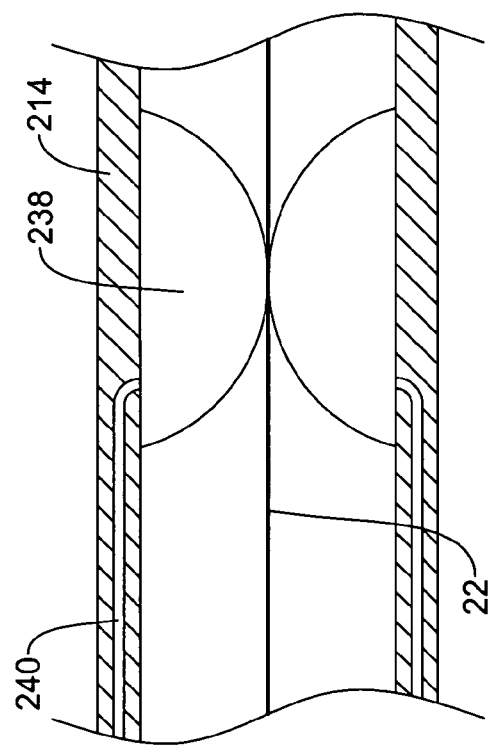
FIG. 7 is a partial cross-sectional side view of the illustrative locking member of FIG. 6 where the locking member is securing the position of a medical device.
Figure 6:
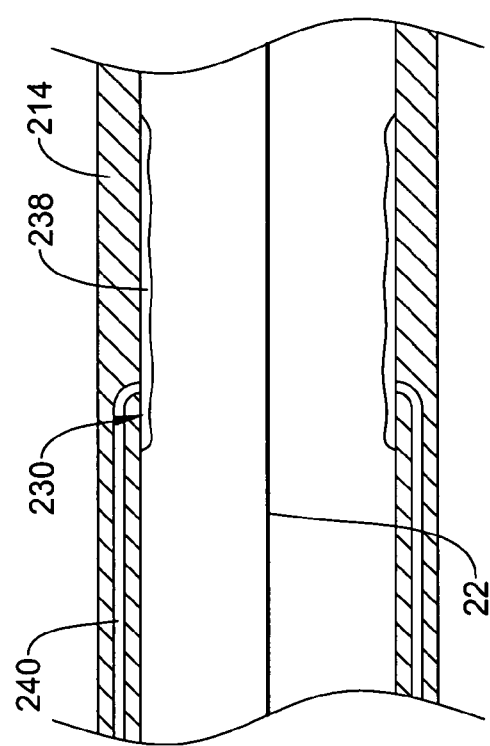
FIG. 6 is a partial cross-sectional side view of another illustrative locking member of an endoscopic instrument assembly.

FIGS. 6 and 7 illustrate another example endoscope locking member 230 that is similar in form and function to locking member 130. Locking member 230 includes inflatable balloon 238 and one or more inflation conduits 240 in fluid communication with balloon 238. Conduit 240, rather than being disposed along the inside surface of shaft portion 214, is formed within the wall of shaft portion 214. This embodiment functions essentially the same as the embodiment shown in FIGS. 4-5.

Figures 8, 9:
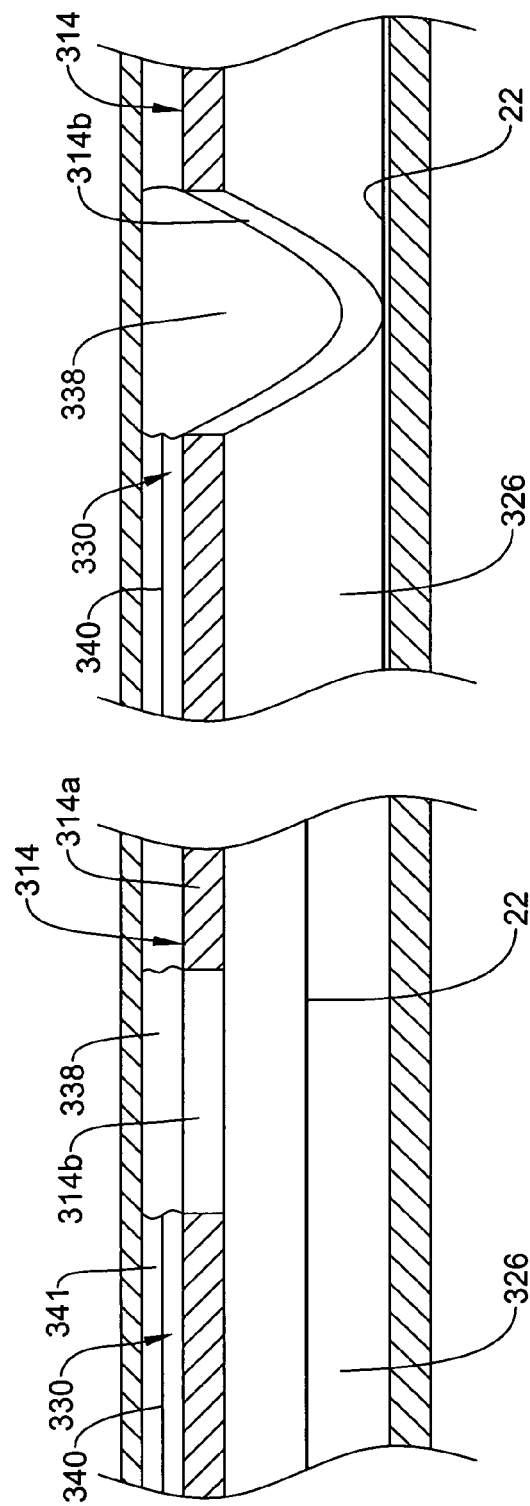
FIG. 8 is a partial cross-sectional side view of another illustrative locking member of an endoscopic instrument assembly.
FIG. 9 is a partial cross-sectional side view of the illustrative locking member of FIG. 8 where the locking member is securing the position of a medical device.

FIGS. 8-9 illustrate another example endoscope locking member 330 that utilizes inflatable balloon 338 and conduit 340. Balloon 338 and conduit 340 are both disposed within the wall of shaft portion 314 (e.g., a secondary lumen 341 formed in the wall of shaft portion 314). In at least some embodiments, the wall of shaft portion 314 is reinforced with a reinforcing structure such as a braid or coil. Reinforced shaft portion 314a thus helps to provide column strength to shaft portion 314 and/or otherwise contributes to the overall integrity of shaft portion 314. In some embodiments, an unreinforced region 314b of shaft portion 314 may be defined that does not include the reinforcement structure. Balloon 338 may be disposed adjacent unreinforced region 314b so that when balloon 338 is inflated, balloon 338 exerts a force onto unreinforced region 314b sufficient to deflect unreinforced region 314b into working channel 326 and secure the position of guidewire 22 as shown in FIG. 9.

The exact form of locking member 330 can vary. For example, a hydraulic mechanism may be utilized to deflect unreinforced region 314b instead of inflating balloon 338. This embodiment functions similar to how a hydraulic braking system functions in automobiles. In addition, unreinforced region 314b (as well as the region of shaft portion 314 directly opposite therefrom) may have a surface modification that alters its shape so that a "clamp" or similarly configured structural arrangement can be formed that assists the locking of guidewire 22. Numerous shapes and arrangements for this type of configuration are contemplated. For example, region 314b may include one or more ridges.

Figure 11:
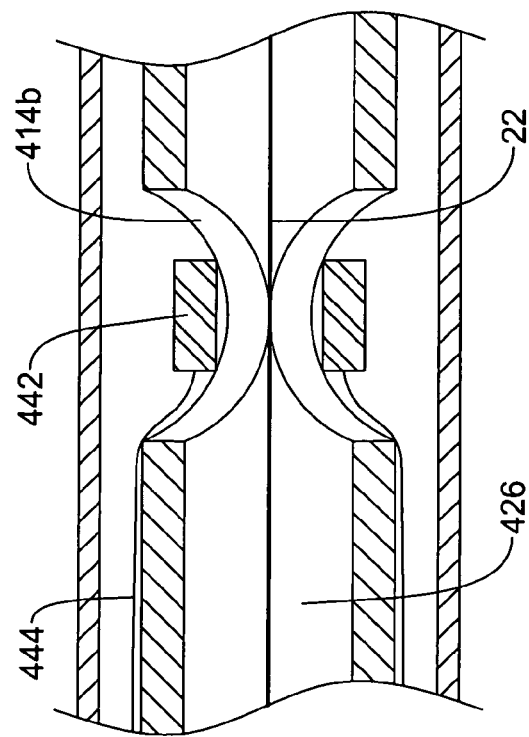
FIG. 11 is a partial cross-sectional side view of the illustrative locking member of FIG. 10 where the locking member is securing the position of a medical device.
Figure 10:
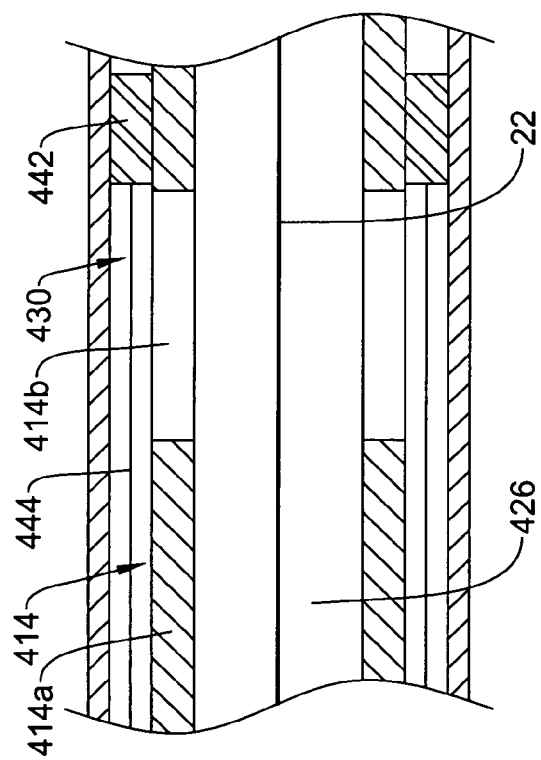
FIG. 10 is a partial cross-sectional side view of another illustrative locking member of an endoscopic instrument assembly.

Another example endoscope locking member 430 is shown in FIGS. 10-11. Locking member 430 includes a clamp member 442 coupled to a pull wire 444. Locking member 430 may be mounted on the exterior of shaft portion 414 or within the wall of shaft portion (as shown). In some embodiments, shaft portion 414 includes both reinforced region 414a and unreinforced region 414b. Clamp member 442 may take the form of a compression ring or compression spring that generally exerts an inward force on shaft portion 414. The force exerted by clamp member 442 is not sufficient to deflect reinforced region 414a, but it is sufficient to deflect unreinforced region 414b. Thus, pull wire 444 can be withdrawn to displace clamp member 442 from a position adjacent reinforced region 414a to a position adjacent unreinforced region 414b, thereby deflecting unreinforced region 414b into working channel 426 to lock guidewire 22 as shown in FIG. 11. Unlocking guidewire 22 may include further retracting pull wire 444 so that clamp member 442 becomes disposed adjacent reinforced region 414a or distally pushing clamp member 442 back to its original position.

Figure 13:
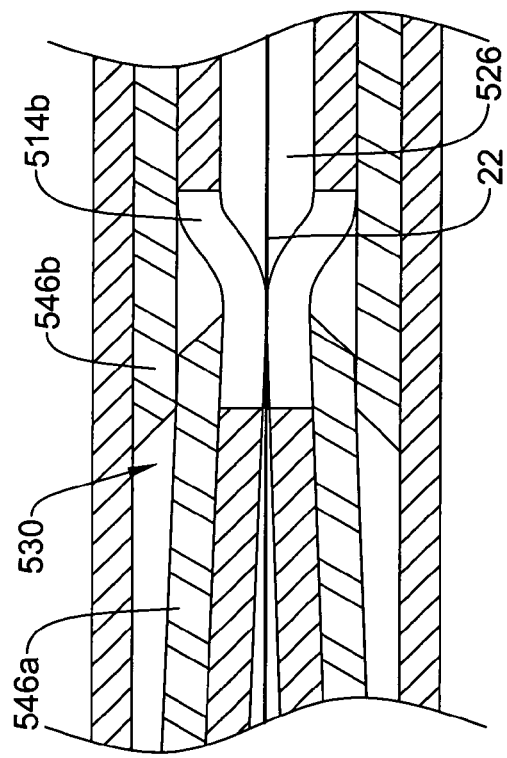
FIG. 13 is a partial cross-sectional side view of the illustrative locking member of FIG. 12 where the locking member is securing the position of a medical device.
Figure 12:
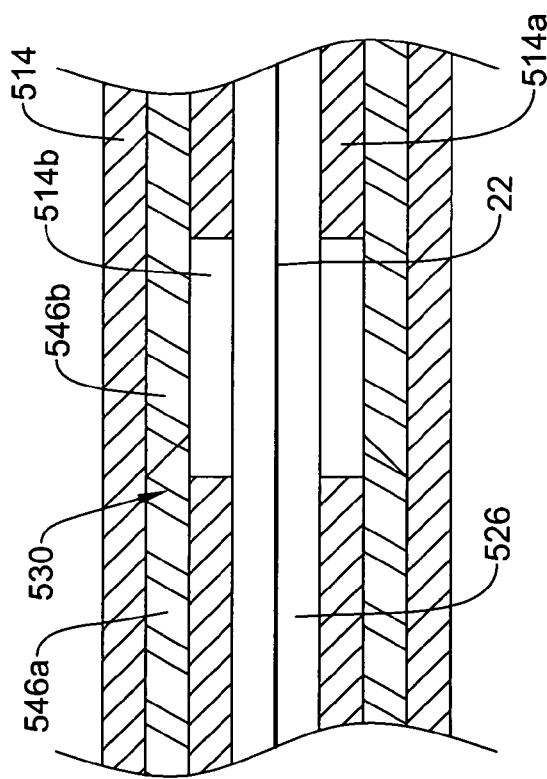
FIG. 12 is a partial cross-sectional side view of another illustrative locking member of an endoscopic instrument assembly.

Another example endoscope locking member 530 is depicted in FIGS. 12-13. Locking member 530 includes a pair of sloped wedge members 546a/546b. One of the wedge members 546a is movable within the wall of shaft portion 514. The other wedge member 546b is fixed relative to the wall of shaft portion 514. Locking member 530 is actuated by pushing wedge member 546a distally so the sloped edges of wedge members 546a/546b cause wedge member 546a to exert force inward onto unreinforced region 514b. This deflects unreinforced region 514b of shaft portion 514 into channel 526, thereby securing the position of guidewire 22. Alternatively, wedge member 546b can be coupled to a pull wire so that member 546b can be proximally retracted to create the same effect. It can be appreciated that a number of differently configured wedge members 546a/546b are contemplated that can generate sufficient force to deflect unreinforced region 514b of shaft portion 514.

Another example endoscope locking member 630 is depicted in FIGS. 14-15. Locking member 630 is similar to locking member 530. As shown in FIGS. 14-15, wedge members 646a/646b are disposed along the interior wall of shaft portion 614 so that actuating wedge member 646a displaces wedge member 646a directly onto guidewire 22.

Another example endoscope locking member 730 is depicted in FIGS. 16-17. Locking member 730 includes a hinged clamp member 742 coupled to a pull wire 744. Hinge 748, which connects clamp member 742 to shaft portion 714 is biased to be deflected inward into working channel 726 (as shown in FIG. 17) by a spring or similar means. Proximally pulling pull wire 744 exerts enough force to overcome the bias and shift clamp member 742 into alignment with shaft portion 714 (as shown in FIG. 16). Thus, a clinician can secure the position of guidewire 22 by allowing hinge 748 to force closed clamp member 742. This may include gently urging pull wire 744 in the distal direction.

In some embodiments, locking member 730 is disposed along an exterior surface of shaft portion 714. In other embodiments, locking member 730 may be disposed within the wall of shaft portion 714. This later embodiment is illustrated via a phantom line 750 drawn in FIGS. 16-17 that represents the outer wall of shaft portion 714.

Figure 19:
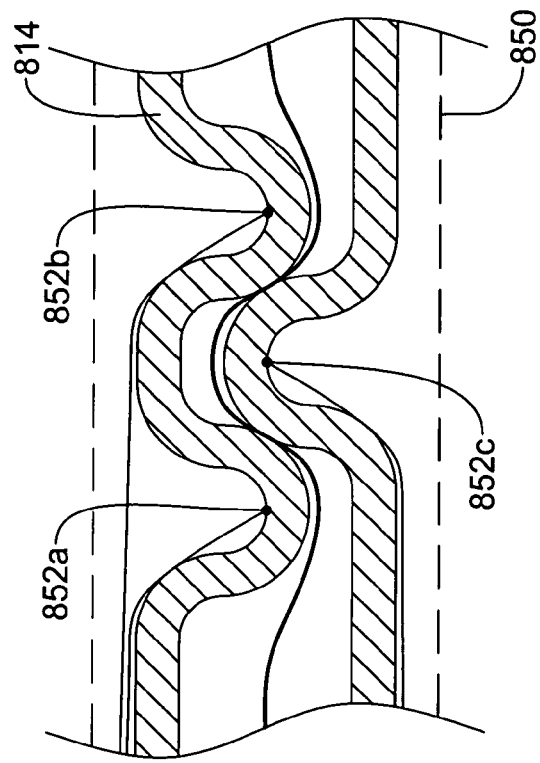
FIG. 19 is a partial cross-sectional side view of the illustrative locking member of FIG. 18 where the locking member is securing the position of a medical device.
Figure 18:
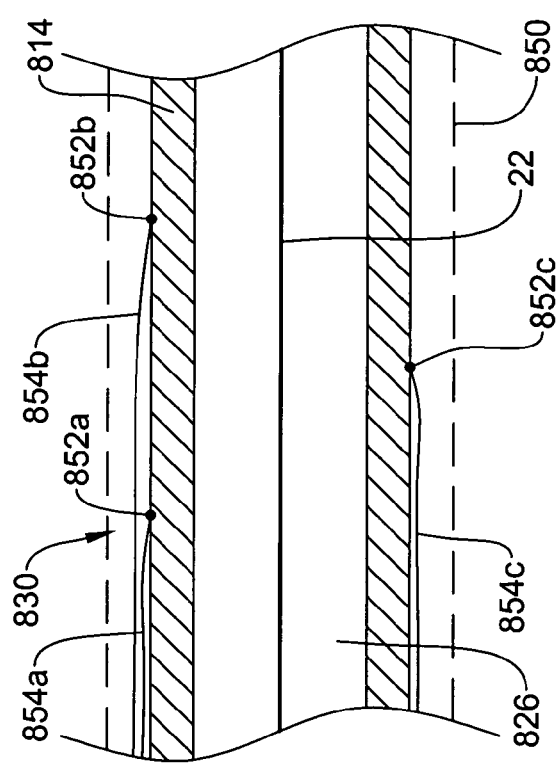
FIG. 18 is a partial cross-sectional side view of another illustrative locking member of an endoscopic instrument assembly.

Endoscope locking member 830 is depicted in FIGS. 18-19. Locking member 830 includes a plurality of clamping members 852a/852b/852c, each having a wire 854a/854b/854c coupled thereto. Clamping members 852a/852b/852c and wires 854a/854b/854c may be disposed along the exterior of shaft portion 814 or may be disposed within the wall of shaft portion 814 as depicted by phantom line 850. Clamping members 852a/852b/852c may be actuated in a number of ways in order to secure the position of guidewire 22. For example, in some embodiments, clamping members 852a/852b/852c form an electric pin vise that is activated by sending current down wires 854a/854b/854c. Upon activation, clamping members 852a/852b/852c are drawn together to secure guidewire 22. Alternatively, clamping members 852a/852b/852c may be magnetized (e.g., clamping members 852a/852b/852c include electromagnets) so that activation of clamping members 852a/852b/852c secures guidewire 22.

Another example endoscope locking member 930 is shown in FIGS. 20-21. Locking member 930 takes the form of an elongated wedge that can advance through a lumen 941 formed in shaft portion 914. Locking member 930 is actuated by advancing it distally within lumen 941 so that it can exert force inward onto shaft portion 914. This deflects shaft portion 914 into channel 926, thereby securing the position of guidewire 22 as seen in FIG. 21.

In at least some embodiments, the locking of guidewire 22 with locking member 930 may also be aided by structural modifications of shaft portion 914. For example, shaft portion 914 may include one or more reinforced regions and one or more unreinforced regions, which may be similar to others disclosed herein. According to these embodiments, locking member 930 may deflect shaft portion 914 when it is positioned adjacent to one of the unreinforced regions. In other embodiments, lumen 941 may have a "wedge-like" or narrowing shape so that a mandrel or shaft locking member can be advanced therein to lock guidewire 22.

FIGS. 22-23 illustrate another example endoscope locking member 1030. Locking member 1030 may include a stent-like or cage-like section 1038 and an actuation wire 1040 coupled thereto. Stent-like section 1038 may be configured to constrict shaft portion 1014. For example, stent-like section 1030 may constrict shaft portion 1014 when actuation wire 1040 is pulled in the proximal direction. To assist this constriction, stent-like section 1030 may have a pull ring (not shown) disposed at one or both of its ends. When stent-like section 1030 constricts shaft portion 1014, shaft portion 1014 deflects into channel 1026 and locks guidewire 22 as shown in FIG. 23.

Numerous variations are contemplated for the configuration of locking member 1030. For example, stent-like section 1038 may take the form of a coil, braid, helix, or any other suitable structure that, when actuated, constricts shaft portion 1014. In additional embodiments, stent-like section 1038 may be made from a shape memory material (e.g., like nickel-titanium alloy, shape memory polymer, etc.) that is "trained" to have a shape suitable for constricting shaft portion 1014 at a certain temperature. In some embodiments, stent-like section 1038 can be heated (e.g., by delivering electrical current to stent-like section 1038 along wire 1040 or in any other manner) to the pre-set temperature, which causes the shape memory locking member 1030 to return to the pre-set shape and lock guidewire 22. Any other of the locking members disclosed herein, to the extent applicable, may similarly utilize shape memory materials in their functioning. Various other mechanisms are also contemplated for actuating locking member 1030 or any of the other locking members disclosed herein including servomechanisms.

Shaft portion 1014 may also include structural features described for any of the other shaft portions disclosed herein. For example, a lumen (not shown) may be formed in the wall of shaft portion 1014. In some of these embodiments, locking member 1030 may be disposed in the lumen. In others, locking member 1030 is disposed along the exterior of shaft portion 1014. Shaft portion 1014 may also include reinforced and/or unreinforced regions that may be similar in form and function to others disclosed herein.

Another example endoscope locking member 1130 is shown in FIGS. 24-25. Locking member 1130 includes an expandable or elastic "brake" 1138 disposed along an interior wall surface of shaft portion 1114. Brake 1138 is configured to shift between a collapsed configuration and an expanded configuration. In at least some embodiments, brake 1138 may be held in the collapsed configuration by a sleeve or covering 1156. Sleeve 1156 may be proximally retracted within channel 1126, thereby allowing brake 1138 to expand into channel 1126 so as to lock guidewire 22 as seen in FIG. 25.

A variety of brakes are contemplated that resemble brake 1138 in form and function. For example, brakes are contemplated that extend around the full circumference of shaft portion 1114, while others extend along only a portion. In addition, the length and/or shape of the brakes may vary. For example, FIG. 26 illustrates locking member 1230 with a brake 1238 that has an increased longitudinal length (i.e., is "long") along shaft portion 1214. Conversely, FIG. 27 illustrates locking member 1330 with a brake 1338 that has a shortened longitudinal length (i.e., is "short") along shaft portion 1314. It can be appreciated that essentially any length of brake may be utilized without departing from the spirit of the invention. FIGS. 28-29 illustrate that any suitable number of brakes (e.g., 1, 2, 3, 4, 5, or more) may be utilized along with a number of different configurations. For example, FIG. 28 depicts locking member 1430 having two brakes 1438a/1438b. Brakes 1438a/1438b can be disposed along the same section of shaft portion 1414 (e.g., they longitudinally align) as shown in FIG. 28. Conversely, FIG. 29 depicts locking member 1530 having two brakes 1538a/1538b disposed on opposing sides of shaft portion 1514. Thus, not only can the number of brakes vary, the position of the various brakes relative to one another can also vary.

FIGS. 30-31 illustrate another example endoscope locking member 1630 disposed adjacent shaft portion 1614. Locking member 1630 includes a sleeve 1656 having an expandable region 1638 formed therein. Expandable region 1638 is configured to buckle and/or expand into channel 1626 to lock guidewire 22 as shown in FIG. 31. For example, sleeve 1656 can be distally advanced to cause expandable region 1638 to buckle.

Expandable region 1638 may be configured to buckle in any of a number of different ways. For example, expandable region 1638 may have a number of pre-formed bends or bendable regions that renders expandable region 1638 amenable to shifting from a longitudinally straight configuration to the buckled configuration. Essentially any other suitable mechanism may be utilized for shifting expandable region 1638 into the buckled configuration.

Another example endoscope locking member 1730 is shown in FIGS. 32-33. Locking member 1730 takes the form of a twistable region formed in shaft portion 1714. Accordingly, twisting shaft portion 1714 shifts the arrangement of the walls of shaft portion 1714 so that a region extends into or otherwise pinches channel 1726 and locks guidewire 22 as shown in FIG. 33.

It should be understood that this disclosure is, in many respects, only illustrative. Changes may be made in details, particularly in matters of shape, size and arrangement of steps without exceeding the scope of the disclosure. The invention's scope is, of course, defined in the language in which the appended claims are expressed.

What is claimed is:

1. A medical device assembly, comprising:
   an elongate shaft having a working channel defined by a tubular member and for receiving a first medical device;
   a single inflatable locking member disposed adjacent a distal end region of the working channel and being configured to selectively secure and unsecure a position of the first medical device in a location when received within the working channel, wherein the single inflatable locking member is axially immovable relative to the elongate shaft, wherein the single inflatable locking member includes a single inflatable balloon; and
   a secondary channel formed within a wall of the tubular member, wherein the secondary channel houses the single inflatable locking member and an inflation lumen to inflate the single inflatable locking member, wherein the working channel is defined by an inner surface of the wall,
   wherein the wall at the distal end region of the working channel includes a first portion reinforced with a reinforcing structure and a second portion adjacent the first portion and devoid of the reinforcing structure, and wherein the single inflatable locking member is disposed at a same axial position as, and radially outside of, the second portion, and wherein, when the single inflatable locking member is inflated, the single inflatable locking member contacts the second portion and forces the second portion radially inward to contact the first medical device and press the first medical device against a portion of the inner surface opposite the second portion.

2. The medical device assembly of claim 1, wherein the shaft includes a distal port disposed adjacent a distal end of the shaft.

3. The medical device instrument assembly of claim 2, wherein the distal port is disposed in a side wall of the shaft portion.

4. The medical device assembly of claim 3, further comprising an elevator coupled to the shaft and disposed within the distal port.

5. The medical device assembly of claim 1, wherein the first medical device is a guidewire.

6. The medical device assembly of claim 1, wherein the first medical device is a catheter.

7. The medical device assembly of claim 1, further comprising a second medical device disposed in the working channel.

8. The medical device assembly of claim 1, wherein the tubular member is a single-piece tubular member.

9. The medical device assembly of claim 1, wherein the single inflatable locking member is positioned completely within the wall of the tubular member.

10. The medical device assembly of claim 9, wherein, when the single inflatable locking member is inflated, the single inflatable locking member radially deflects the second portion of the wall towards the medical device.

11. The medical device assembly of claim 10, wherein the medical device is secured between the second portion of the wall and the inner surface of the wall when the single inflatable locking member is inflated.

12. The medical device assembly of claim 1, wherein the first portion is both distal and proximal the second portion.

13. The medical device assembly of claim 12, wherein the first portion has a column strength greater than a column strength of the second portion.

14. The medical device assembly of claim 1, wherein the reinforcing structure is one of a braid and a coil.

15. The medical device assembly of claim 1, wherein the single inflatable locking member is a discrete structural element from the wall.

16. The medical device assembly of claim 1, wherein, when the single inflatable locking member is in an uninflated state, the first portion and the second portion are located at a same radial position.

17. A medical device assembly, comprising:
    a shaft having a distal end region and a working channel defined by a tubular member for receiving a medical device therein;
    a single inflatable locking member disposed within the distal end region and being adapted to shift between a first configuration where the single inflatable locking member substantially locks the medical device in a position and a second configuration where the medical device is movable within the working channel, wherein the single inflatable locking member includes a single inflatable balloon; and
    a secondary channel formed within a wall of the tubular member, wherein the secondary channel houses the single inflatable locking member and an inflation lumen to inflate the single inflatable locking member, wherein the working channel is defined by an inner surface of the wall,
    wherein the wall at the distal end region of the shaft includes a first portion reinforced with a reinforcing structure and a second portion adjacent the first portion and devoid of the reinforcing structure, wherein the single inflatable locking member is disposed at a same axial position as, and radially outside of, the second portion, and wherein when the single inflatable locking member is inflated, the single inflatable locking member contacts the second portion and forces the second portion radially inward to contact the medical device and press the medical device against a portion of the inner surface opposite the second portion, wherein the single inflatable locking member does not contact the medical device.

18. The medical device assembly of claim 17, further comprising an elevator coupled to the shaft and disposed within a distal port defined on a side wall of the shaft and in fluid communication with the working channel.

19. The medical device assembly of claim 17, wherein the tubular member is a single-piece tubular member.

20. The medical device assembly of claim 17, wherein the first portion is both distal and proximal the second portion.

21. The medical device assembly of claim 20, wherein the first portion has a column strength greater than a column strength of the second portion.

22. The medical device assembly of claim 17, wherein the reinforcing structure is one of a braid and a coil.

23. The medical device assembly of claim 17, wherein the single inflatable locking member is a discrete structural element from the wall.

24. The medical device assembly of claim 17, wherein the single inflatable locking member is internal the wall of the tubular member.

* * * * *